United States Patent [19]
Davidson et al.

[11] Patent Number: 5,700,460
[45] Date of Patent: *Dec. 23, 1997

[54] METHODS OF ATTRACTING AND COMBATTING INSECTS

[75] Inventors: Thomas Charles Davidson, Durham; Georgina M. Werner, Raleigh, both of N.C.

[73] Assignee: Rhone-Poulenc Inc., Research Triangle Park, N.C.

[*] Notice: The term of this patent shall not extend beyond the expiration date of Pat. No. 5,614,182.

[21] Appl. No.: 731,132

[22] Filed: Oct. 10, 1996

Related U.S. Application Data

[63] Continuation-in-part of Ser. No. 419,609, Apr. 10, 1995, Pat. No. 5,614,182 and a continuation-in-part of PCT/EP96/01334, Mar. 27, 1996.

[51] Int. Cl.$^6$ .................................................. A01N 25/00
[52] U.S. Cl. .................. 424/84; 514/347; 514/351; 514/357; 514/404; 514/407
[58] Field of Search ..................... 424/84; 514/347, 514/351, 357, 404, 407

[56] References Cited

U.S. PATENT DOCUMENTS

| | | | |
|---|---|---|---|
| 4,985,413 | 1/1991 | Kohama et al. | 514/79 |
| 5,152,992 | 10/1992 | Kandathil et al. | 424/405 |
| 5,232,940 | 8/1993 | Hatton et al. | 514/407 |
| 5,236,938 | 8/1993 | Huang et al. | 514/341 |
| 5,256,679 | 10/1993 | Minamida et al. | 514/357 |
| 5,306,694 | 4/1994 | Phillips et al. | 504/253 |
| 5,482,955 | 1/1996 | Jautelat et al. | 514/383 |

FOREIGN PATENT DOCUMENTS

| | | |
|---|---|---|
| 0295117 | 12/1988 | European Pat. Off. . |
| 0385809 | 9/1990 | European Pat. Off. . |
| 0403300 | 12/1990 | European Pat. Off. . |
| 0500209 | 8/1992 | European Pat. Off. . |
| 0679650 | 11/1995 | European Pat. Off. . |
| 19511269 | 10/1995 | Germany . |
| 87/03781 | 7/1987 | WIPO . |
| 93/06089 | 4/1993 | WIPO . |
| 94/21606 | 9/1994 | WIPO . |
| 96/17515 | 6/1996 | WIPO . |

*Primary Examiner*—Brian M. Burn
*Attorney, Agent, or Firm*—Burns, Doane, Swecker & Mathis, L.L.P.

[57] ABSTRACT

A method for attracting and controlling insects comprising offering to said insects for ingestion an effective amount of a compound of the formula:

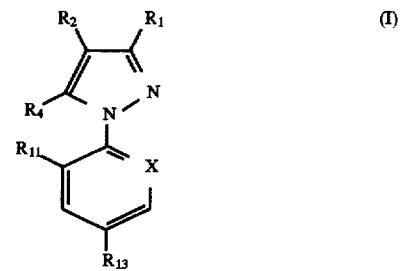

wherein the structural variables are as defined in the specification.

36 Claims, No Drawings

METHODS OF ATTRACTING AND COMBATTING INSECTS

CROSS-REFERENCE TO RELATED APPLICATIONS

This application is a continuation-in-part of U.S. patent application Ser. No. 08/419,609, filed Apr. 10, 1995, and a continuation-in-part of International Patent Application No. PCT/EP96/01334, filed Mar. 27, 1996 and designating the United States. Both of said earlier applications are incorporated by reference herein in their entireties and relied upon.

BACKGROUND OF THE INVENTION

1. Field of the Invention

The invention relates to methods of attracting and combatting insects at a locus at which a crop is growing, especially a plantation crop, or at a locus where the presence of insects is undesirable for public health reasons.

2. Description of the Related Art

Many insecticidally active compounds are known, such as the insecticidal pyrazoles described in International Patent Publications No. WO 87/03781, WO 93/06089 and WO 94/21606, as well as in European Patent Publications No. 0295117, 0403300, 0385809, 0500209 and 0679650, German Patent Publication No. 19511269 and U.S. Pat. Nos. 5,232,940, 5,236,938 and 5,306,694, all of which are incorporated by reference herein in their entireties and relied upon, in particular for their descriptions of compounds of formulas (I) and (Ia) set forth hereinafter, generally and specifically, and for their descriptions of processes for the preparation and insecticidal use of such compounds.

A particular problem connected with the control of nuisance insects, especially the insects which are found to inhabit private or public housing or buildings, is that it is difficult to reach and treat all of the insects and it is most desirable to have a method to eliminate the population of insects, especially those insects which are not accessible to the treatment or have remained untreated for any reason.

An additional obstacle in eliminating or reducing a population of nuisance insects is that said insects are often able to detect the presence of insecticidally active ingredients, said ingredients thus acting as a repellent or anti-feeding agent for the insects.

Up until now, a common method for controlling a large population of insects, especially those inaccessible to direct treatment, is to utilize a program of multiple treatments or multiple placement of baits containing insecticidally active ingredients, or to associate attractants with insecticidally active ingredients.

OBJECTS AND SUMMARY OF THE INVENTION

An object of the instant invention is to provide a simplified and efficient method of controlling or combatting insects.

Another object of the instant invention is to provide a simplified and efficient method of controlling or combatting insects whereby an attractive ingredient, that is, an attractant, is presented to the insects.

An especially advantageous object of the instant invention is to provide a simplified and efficient method of controlling or combatting insects whereby an attractant is presented to the insects, said attractant being simultaneously insecticidally active.

The present invention thus provides a new use, as an attractant for insects, of a compound having the formula:

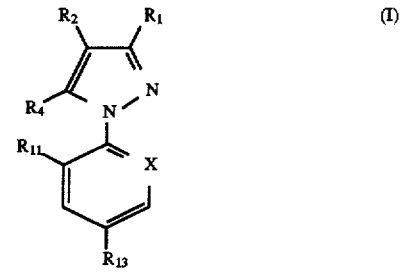

(I)

wherein:

$R_1$ is CN or methyl;

$R_2$ is $S(O)_n R_3$;

$R_3$ is alkyl or haloalkyl;

$R_4$ is hydrogen, halogen, $-NR_5 R_6$, $-S(O)_m R_7$, alkyl, haloalkyl, $-OR_8$ or $-N=C(R_9)(R_{10})$;

each of $R_5$ and $R_6$, which are the same or different, is hydrogen, alkyl, haloalkyl, $-C(O)$alkyl or $-S(O)_r CF_3$; or $R_5$ and $R_6$ together a divalent lower alkylene radical which is optionally interrupted by one or more heteroatoms (O, S or N);

$R_7$ is alkyl or haloalkyl;

$R_8$ is alkyl, haloalkyl or hydrogen;

$R_9$ is hydrogen or alkyl;

$R_{10}$ is phenyl or heteroaryl, each of which is unsubstituted or is substituted with one or more substituents selected from the group consisting of hydroxy, halogen, $-O-$alkyl, $-S-$alkyl, cyano and alkyl;

each of $R_{11}$ and $R_{12}$, which are the same or different, is halogen or hydrogen;

$R_{13}$ is halogen, haloalkyl, haloalkoxy, $-S(O)_q CF_3$ or $-SF_5$;

each of m, n, q and r, which are the same or different, is 0, 1 or 2; and

X is nitrogen or C—$R_{12}$;

provided that when $R_1$ is methyl, $R_3$ is haloalkyl, $R_4$ is $NH_2$, $R_{11}$ is Cl, $R_{13}$ is $CF_3$ and X is N.

In one particular aspect, the present invention provides a new use, as an attractant for insects, of a compound having the formula:

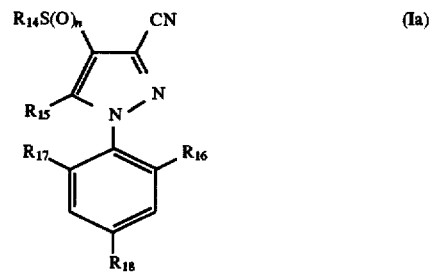

(Ia)

wherein:

$R_{14}$ is alkyl or haloalkyl;

$R_{15}$ is alkyl, haloalkyl, amino, alkylamino or dialkylamino;

each of $R_{16}$ and $R_{17}$, which are the same or different, is hydrogen or halogen, at least one of them preferably being other than hydrogen;

$R_{18}$ is halogen, haloalkyl, haloalkoxy or $SF_5$; and n is 0, 1 or 2.

In another aspect, the present invention provides a method for attracting insects, said method comprising offering to said insects for ingestion an effective attractant amount of a compound of formula (I) or (Ia) as defined above.

In yet another aspect, the present invention provides a method for attracting and killing insects comprising offering to said insects for ingestion a compound of formula (I) or (Ia) as defined above in an amount which is effective both as an attractant and as an insecticide.

DETAILED DESCRIPTION OF THE INVENTION

In the present description, the following definitions are applicable:

The alkyl radicals and the alkyl portions of other radicals (e.g. the haloalkyl, haloalkoxy, alkylamino and dialkylamino radicals) can have up to six carbon atoms but are preferably lower alkyl, that is to say, they preferably each have one to four carbon atoms. In the case of the dialkylamino radicals, the alkyl portions can be the same or different. The alkyl radicals and alkyl portions of other radicals can be straight- or branched-chain. The halogen atoms can be fluorine, chlorine, bromine or iodine, preferably fluorine or chlorine.

When $R_5$ and $R_6$ in formula (I) together form a divalent lower alkylene ($C_3$-$C_7$) radical optionally interrupted by one or more heteroatoms, $-NR_5R_6$ preferably represents piperidino, piperazinyl, morpholino, thiomorpholino, pyrrolidino or hexamethyleneimino, each of which is optionally substituted with one or more lower alkyl groups.

When $R_{10}$ in formula (I) is heteroaryl, it is preferably pyridyl, pyrimidinyl, pyridazinyl, pyrazinyl, thiazolyl, benzothienyl, benzofuryl, quinolyl, isoquinolyl, benzothiazolyl or methylenedioxyphenyl, each of which is optionally substituted as indicated with the definition of $R_{10}$ hereinabove.

A preferred group of compounds of formula (I) for use herein are those in which:

$R_1$ is CN; and/or $R_3$ is haloalkyl; and/or $R_4$ is $NH_2$; and/or each of $R_{11}$ and $R_{12}$, which are the same or different, is halogen; and/or $R_{13}$ is haloalkyl.

Preferred compounds of formula (Ia) for use in accord with the present invention are compounds in which each of $R_{16}$ and $R_{17}$ is a halogen atom, $R_{18}$ is a haloalkyl radical, $R_{14}$ is a lower haloalkyl radical and $R_{15}$ is an amino radical.

Especially preferred for use in accord with the present invention is the insecticide known as fipronil, whose chemical name is 5-amino-3-cyano-1-(2,6-dichloro-4-trifluoromethyl)phenyl-4-trifluoromethylsulfinylpyrazole, and which is specifically described in the aforementioned EP 0295117 and Hatton et al U.S. Pat. No. 5,232,940.

The preparation of compounds of formula (I), such as the compounds of formula (Ia), for use herein can proceed according to any process described in the hereinabove-cited patent documents, or other process within the knowledge of one skilled in the art of chemical synthesis.

According to a further aspect of the invention, there is provided a method for controlling a population of insects, especially insects able to walk or travel in public or private housing or building or household or home, that is, insects which are able to enter or inhabit buildings, whereby an attractant and insecticidally effective mount of a compound of formula (I) as defined above, such as a compound of formula (Ia), is offered or presented to the insects to be controlled as food among alternative food or foods, which can be closely situated.

The method of the invention is especially advantageous because it provides more possibilities and much more freedom for placement of the insecticidally active ingredient. Because of its attractant properties, the insecticidally active ingredient can be located in any place, not only at the specifically appropriate place where the insects are to travel and feed.

In a preferred embodiment of the present invention, there is provided a method for controlling a population of insects at a locus which is in or near a food storage, preparation, serving or eating area, said method comprising offering to said insects as an alternative food source an mount of a compound of formula (I) as defined above, such as a compound of formula (Ia), which is effective both as an attractant and as an insecticide. Thus, an effective attractant and insecticidal mount of a compound of formula (I), such as a compound of formula (Ia), is preferably offered to the insects in or near an area in which other food is present as a practical consequence of the normal use of the building or housing.

The active ingredient of formula (I)/(Ia) is preferably used in accord with the present invention in the form of a bait, which can be a solid, liquid or gel bait. The manner of preparation of a bait will be apparent to one of ordinary skill in the art. Baits have already been described in the patent documents cited hereinabove. It is of course not necessary to add an attractant to the active ingredient of formula (I)/(Ia) and the carrier or diluent to form the bait, since the compound of formula (I)/(Ia) acts herein as an attractant as well as an insecticide.

The method of the invention is particularly appropriate as a method for the control of populations of insects like cockroaches, ants or the like, especially those belonging to the families Blatidae and Formacidae. Treatment of cockroaches in an area in which their presence can be detrimental to public health, that is to say in housing or buildings, is a preferred feature of the instant invention, especially for the control of so-called American cockroaches (*Periplaneta americana*), but also of other cockroaches such as German cockroaches (*Blatella germanica*).

The attractant compositions or baits which can be used in the practice of the present invention can be offered or presented to the insects in various amounts. Usually, however, it is advantageous to offer these attractant compositions or baits comprising the compound of formula (I)/(Ia) in an appropriate form and in an amount of from about 0.00001 g to about 20 g of active ingredient of formula (I)/(Ia) per 100 square meters, preferably of from about 0.001 g to about 1 g per 100 m$^2$.

The attractant compositions which are useful in the present invention generally comprise from about 0.0001 to about 15 % w/w of active ingredient of formula (I)/(Ia), preferably from about 0.01 to about 6 % w/w. These compositions can be in the form of a solid, e.g. dusts or granules or wettable powders, or in the form of a liquid, such as an emulsifiable concentrate or a true solution.

The attractant compositions can also contain any compatible surface-active agent and/or carrier, preferably selected from ingredients which can be eaten by insects. The carrier itself can be solid or liquid.

The compounds of formula (I)/(Ia) can be used in sequence or admixture, particularly in admixtures with another pesticide, for example, an insecticide, acaricide or fungicide.

The attractant compositions can be prepared by simply admixing the ingredients.

The invention is illustrated by the following examples which should not be considered as limiting or restricting the invention.

EXAMPLES

On a large circle situated on a 1 square meter confinement, various foodstuffs and two baits of fipronil were distributed around the perimeter of a circle of 75 cm diameter. Similar pieces of baits were placed at diametrically opposed points on the circle.

Adults cockroaches (25 males and 25 females) were released and offered harborage 24 hours prior to the start of the experiment. All testing was conducted at night under infrared illumination. Three replicates were conducted for each species. Observations began one hour after lighting in the laboratory went off. The number of foraging cockroaches at each location was recorded at 10 minute intervals for a period of 120 minutes.

Example 1

Only fipronil was used as an insecticide.

The alternative foods were: 2 pieces of rodent chow, 2 pieces of rodent jelly and 2 vials of water.

The numbers of foraging German cockroaches for up to 3 hours of foraging time were measured and cumulatively added.

62 cockroaches went to fipronil, 43 to chow, 25 to jelly and 22 to water.

Example 2

Only fipronil was used as an insecticide.

The alternative foods were: 2 pieces of rodent chow, 2 vials of oil and 2 vials of water.

The numbers of foraging German cockroaches for up to 3 hours of foraging time were measured and cumulatively added.

68 cockroaches went to fipronil, 25 to chow, 23 to oil and 14 to water.

Example 3

One insecticidal bait comprised fipronil and one comprised hydramethylnon.

The alternative foods were: 2 pieces of rodent chow, 2 pieces of rodent jelly, 2 vials of water and 1 piece of hydramethylnon.

The numbers of foraging American cockroaches for up to 3 hours of foraging time were measured and cumulatively added.

35 cockroaches went to fipronil (substantially less to the other insecticide), 17 to chow, 15 to jelly and 18 to water.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method for attracting insects, said method comprising offering to said insects for ingestion an effective attractant amount of a compound having the formula:

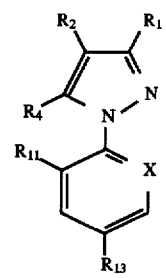

wherein $R_1$ is CN or methyl;

$R_2$ is $-S(O)_nR_3$;

$R_3$ is alkyl or haloalkyl;

$R_4$ is hydrogen, halogen, $-NR_5R_6$, $-S(O)_mR_7$, alkyl, haloalkyl, $-OR_8$ or $-N=C(R_9)(R_{10})$;

each of $R_5$ and $R_6$, which are the same or different, is hydrogen, alkyl, haloalkyl, $-C(O)$alkyl or $-S(O)_rCF_3$; or $R_5$ and $R_6$ together form a divalent lower alkylene radical which is optionally interrupted by one or more heteroatoms selected from O, S and N;

$R_7$ is alkyl or haloalkyl;

$R_8$ is alkyl, haloalkyl or hydrogen;

$R_9$ is hydrogen or alkyl;

$R_{10}$ is phenyl or heteroaryl, each of which is unsubstituted or is substituted with one or more substituents selected from the group consisting of hydroxy, halogen, $-O-$alkyl, $-S-$alkyl, cyano and alkyl;

each of $R_{11}$ and $R_{12}$, which are the same or different, is halogen or hydrogen;

$R_{13}$ is halogen, haloalkyl, haloalkoxy, $-S(O)_qCF_3$ or $-SF_5$;

each of m, n, q and r, which are the same or different, is 0, 1 or 2; and

X is nitrogen or $C-R_{12}$;

provided that when $R_1$ is methyl, $R_3$ is haloalkyl, $R_4$ is $NH_2$, $R_{11}$ is Cl, $R_{13}$ is $CF_3$, and X is N.

2. A method according to claim 1, having at least one feature selected from the group consisting of:

(a) $R_1$ is CN;

(b) $R_3$ is haloalkyl;

(c) $R_4$ is $NH_2$;

(d) each of $R_{11}$ and $R_{12}$, which are the same or different, is halogen; and (e) $R_{13}$ is haloalkyl.

3. A method according to claim 1, wherein said insects are insects which are able to enter or inhabit buildings.

4. A method according to claim 3, wherein said compound of formula (I) is offered to said insects as an alternative food source at a locus which is in or near an area in which other food is present.

5. A method according to claim 4, wherein the food source comprising said compound of formula (I) is in solid, liquid or gel form.

6. A method according to claim 5, wherein said solid, liquid or gel form is a solid, liquid or gel bait.

7. A method according to claim 1, wherein said insects belong to the family Blatidae or Formacidae.

8. A method according to claim 4, wherein said insects are cockroaches.

9. A method according to claim 1, wherein said insects are American cockroaches (*Periplanipa americana*) or German cockroaches (*Blatella germanica*).

10. A method according to claim 6, wherein said insects are American cockroaches (*Periplanipa americana*) or German cockroaches (*Blatella germanica*).

11. A method according to claim 4, wherein said compound of formula (I) is offered in an mount of from about 0.00001 g to about 20 g per 100 square meters.

12. A method according to claim 11, wherein said compound of formula (I) is offered in an mount of from about 0.001 g to about 1 g per 100 square meters.

13. A method according to claim 4, wherein the food source comprising said compound of formula (I) comprises from about 0.001 to about 15 % w/w of compound of formula (I).

14. A method according to claim 13, wherein the food source comprising said compound of formula (I) comprises from about 0.1 to about 6 % w/w of compound of formula (I).

15. A method for attracting and killing insects comprising offering to said insects for ingestion a compound having the formula:

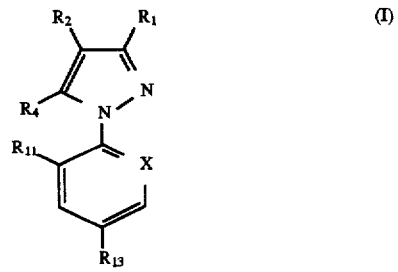

(I)

wherein:

$R_1$ is CN or methyl;

$R_2$ is $S(O)_nR_3$;

$R_3$ is alkyl or haloalicyl;

$R_4$ is hydrogen, halogen, $-NR_5R_6$, $-S(O)_mR_7$, alkyl, haloalkyl, $-OR_8$ or $-N=C(R_9)(R_{10})$;

each of $R_5$ and $R_6$, which are the same or different, is hydrogen, alkyl, haloalkyl, -C(O)alkyl or -S(O)$_r$CF$_3$; or $R_5$ and $R_6$ together form a divalent lower alkylene radical which is optionally interrupted by one or more heteroatoms selected from O, S and N;

$R_7$ is alkyl or haloalkyl;

$R_8$ is alkyl, haloalkyl or hydrogen;

$R_9$ is hydrogen or alkyl;

$R_{10}$ is phenyl or heteroaryl, each of which is unsubstituted or is substituted with one or more substituents selected from the group consisting of hydroxy, halogen, —O—alkyl, —S—alkyl, cyano and alkyl;

each of $R_{11}$ and $R_{12}$, which are the same or different, is halogen or hydrogen;

$R_{13}$ is halogen, haloalkyl, haloalkoxy, $-S(O)_qCF_3$ or $-SF_5$;

each of m, n, q and r, which are the same or different, is 0, 1 or 2; and

X is nitrogen or C—$R_{12}$;

provided that when $R_1$ is methyl, $R_3$ is haloalkyl, $R_4$ is NH$_2$, $R_{11}$ is C$_1$, $R_{13}$ is CF$_3$, and X is N;

wherein said compound of formula (I) is offered in an amount which is effective both as an attractant and as an insecticide.

16. A method according to claim 15, having at least one feature selected from the group consisting of:

(a) $R_1$ is CN;

(b) $R_3$ is haloalkyl;

(c) $R_4$ is NH$_2$;

(d) each of $R_{11}$ and $R_{12}$, which are the same or different, is halogen; and (e) $R_{13}$ is haloalkyl.

17. A method according to claim 15, wherein said compound of formula (I) is offered to said insects as an alternative food source at a locus which is in or near an area in which other food is offered.

18. A method according to claim 17, wherein the food source comprising said compound of formula (I) is in solid, liquid or gel form.

19. A method according to claim 18, wherein said solid, liquid or gel form is a solid, liquid or gel bait.

20. A method according to claim 15, wherein said insects belong to the family Blatidae or Formacidae.

21. A method according to claim 17, wherein said insects are cockroaches.

22. A method according to claim 15, wherein said insects are American cockroaches (*Periplanipa americana*) or German cockroaches (*Blatella germanica*).

23. A method according to claim 19, wherein said insects are American cockroaches (*Periplanipa americana*) or German cockroaches (*Blatella germanica*).

24. A method according to claim 15, wherein said compound of formula (I) is offered in combination with a carrier or surface-active agent.

25. A method according to claim 15, wherein said compound of formula (I) is offered in combination with another pesticide.

26. A method according to claim 15, wherein said compound of formula (I) is offered in an amount of from about 0.00001 g to about 20 g per 100 square meters.

27. A method according to claim 26, wherein said compound of formula (I) is offered in an amount of from about 0.001 g to about 1 g per 100 square meters.

28. A method according to claim 17, wherein the food source comprising said compound of formula (I) comprises from about 0.001 to about 15 % w/w of compound of formula (I).

29. A method according to claim 28, wherein the food source comprising said compound of formula (I) comprises from about 0.1 to about 6 % w/w of compound of formula (I).

30. A method for controlling a population of insects at a locus which is in or near a food storage, preparation, serving or eating area, said method comprising offering to said insects as an alternative food source an amount of a compound having the formula:

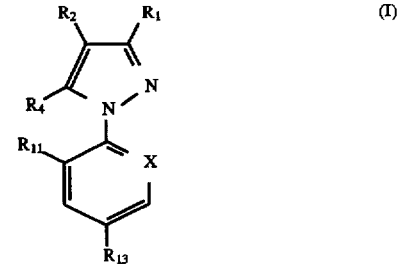

(I)

wherein:

$R_1$ is CN or methyl;

$R_2$ is $-S(O)_nR_3$;

$R_3$ is alkyl or haloalkyl;

$R_4$ is hydrogen, halogen, $-NR_5R_6$, $-S(O)_mR_7$, alkyl, haloalkyl, $-OR_8$ or each of $R_5$ and $R_6$, which are the same or different, is hydrogen, alkyl, haloalkyl, —C(O)alkyl or —S(O)$_r$CF$_3$; or R$_5$ and R$_6$ together form a divalent lower alkylene radical which is optionally interrupted by one or more heteroatoms selected from O, S and N;

R$_7$ is alkyl or haloalkyl;

R$_8$ is alkyl, haloalkyl or hydrogen;

R$_9$ is hydrogen or alkyl;

R$_{10}$ is phenyl or heteroaryl, each of which is unsubstituted or is substituted with one or more substituents selected from the group consisting of hydroxy, halogen, —O—alkyl, —S—alkyl, cyano and alkyl;

each of R$_{11}$ and R$_{12}$, which are the same or different, is halogen or hydrogen;

R$_{13}$ is halogen, haloalkyl, haloalkoxy, —S(O)$_q$CF$_3$ or —SF$_5$;

each of m, n, q and r, which are the same or different, is 0, 1 or 2; and

X is nitrogen or C—R$_{12}$;

provided that when R$_1$ is methyl, R$_3$ is haloalkyl, R$_4$ is NH$_2$, R$_{11}$ is Cl, R$_{13}$ is CF$_3$, and X is N;

which is effective both as an attractant and as an insecticide.

31. A method according to claim 30, having at least one feature selected from the group consisting of:

(a) R$_1$ is CN;

(b) R$_3$ is haloalkyl;

(c) R$_4$ is NH$_2$;

(d) each of R$_{11}$ and R$_{12}$, which are the same or different, is halogen; and (e) R$_{13}$ is haloalkyl.

32. A method according to claim 30, wherein the food source comprising said compound of formula (I) is in solid form.

33. A method according to claim 32, wherein said solid form is a solid bait.

34. A method according to claim 30, wherein said insects are cockroaches.

35. A method according to claim 30, wherein said compound of formula (I) is offered in an amount of from about 0.00001 g to about 20 g per 100 square meters.

36. A method according to claim 35, wherein said compound of formula (I) is offered in an amount of from about 0.001 g to about 1 g per 100 square meters.

* * * * *

(12) EX PARTE REEXAMINATION CERTIFICATE (9856th)
United States Patent
Davidson et al.

(10) Number: US 5,700,460 C1
(45) Certificate Issued: Sep. 27, 2013

(54) METHODS OF ATTRACTING AND COMBATTING INSECTS

(75) Inventors: Thomas Charles Davidson, Durham, NC (US); Georgina M. Werner, Raleigh, NC (US)

(73) Assignee: Bayer Cropscience, LP, Research Triangle Park, NC (US)

Reexamination Request:
No. 90/008,317, Dec. 12, 2006

Reexamination Certificate for:
Patent No.: 5,700,460
Issued: Dec. 23, 1997
Appl. No.: 08/731,132
Filed: Oct. 10, 1996

Related U.S. Application Data

(63) Continuation-in-part of application No. 08/419,609, filed on Apr. 10, 1995, now Pat. No. 5,614,182, and a continuation-in-part of application No. PCT/EP96/01334, filed on Mar. 27, 1996.

(51) Int. Cl.
*A01N 43/56* (2006.01)
*A01N 43/48* (2006.01)
*A01N 47/02* (2006.01)

(52) U.S. Cl.
USPC ............ 424/84; 514/347; 514/351; 514/357; 514/404; 514/407

(58) Field of Classification Search
None
See application file for complete search history.

(56) References Cited

To view the complete listing of prior art documents cited during the proceeding for Reexamination Control Number 90/008,317, please refer to the USPTO's public Patent Application Information Retrieval (PAIR) system under the Display References tab.

*Primary Examiner* — Gary Kunz

(57) ABSTRACT

A method for attracting and controlling insects comprising offering to said insects for ingestion an effective amount of a compound of the formula:

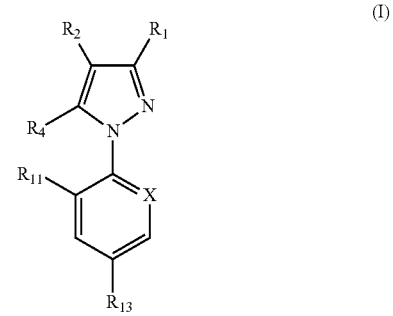

wherein the structural variables are as defined in the specification.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3, 7, 9, 15, 16, 20, 22, 24-27 and 31 are cancelled.

Claims 4-6, 10-14, 17-19, 23, 28-30, 32, 33, 35 and 36 are determined to be patentable as amended.

Claims 8, 21 and 34, dependent on an amended claim, are determined to be patentable.

4. A method according to claim 3, wherein said compound [of formula (I)] is offered to said insects as an alternative food source at a locus which is in or near an area in which other food is present, *wherein said alternative food source does not contain additional attractant components.*

5. A method according to claim 4, wherein the food source comprising said compound [of formula (I)] is in solid, liquid or gel form.

6. A method according to claim 5, wherein said solid, liquid or gel form is a solid, liquid or gel bait, *said bait comprising said compound and ingredients that can be eaten by insects, but said bait does not contain an additional attractant.*

10. A method according to claim 6, wherein said insects are American cockroaches [(Periplanipa americana)] *(Periplaneta americana)* or German cockroaches (Blatella germanica).

11. A method according to claim 4, wherein said compound [of formula (I)] is offered in an [mount] *amount* of from about 0.00001 g to about 20 g per 100 square meters.

12. A method according to claim 11, wherein said compound [of formula (I)] is offered in an [mount] *amount* of from about 0.001 g to about 1 g per 100 square meters.

13. A method according to claim 4, wherein the food source comprising said compound [of formula (I)] comprises from about 0.001 to about 15 % w/w [of compound of formula (I)].

14. A method according to claim 13, wherein the food source comprising said compound [of formula (I)] comprises from about 0.1 to about 6 % w/w [of compound of formula (I)].

17. A method according to claim 15, wherein said compound [of formula (I)] is offered to said insects as an alternative food source at a locus which is in or near an area in which other food is offered; *wherein said alternative food source does not contain an additional attractant component.*

18. A method according to claim 17, wherein the food source comprising said compound [of formula (I)] is in solid, liquid or gel form.

19. A method according to claim 18, wherein said solid, liquid or gel form is a solid, liquid or gel bait, *said bait comprising said compound and ingredients that can be eaten by insects, but said bait does not contain an additional attractant.*

23. A method according to claim 19, wherein said insects are American cockroaches [(Periplanipa americana)] *(Periplaneta americana)* or German cockroaches (Blatella germanica).

28. A method according to claim 17, wherein the food source comprising said compound [of formula (I)] comprises from about 0.001 to about 15 % w/w of compound [of formula (I)].

29. A method according to claim 28, wherein the food source comprising said compound [of formula (I)] comprises from about 0.1 to about 6 % w/w of compound [of formula (I)].

30. A method for controlling a population of insects at a locus which is in or near a food storage, preparation, serving or eating area, said method comprising offering to said insects as an alternative food source an amount of a compound having the formula:

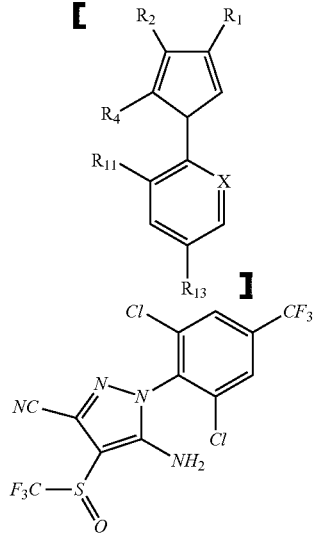

[wherein:
$R_1$ is CN or methyl;
$R_2$ is —$S(O)_n R_3$;
$R_3$ is alkyl or haloalkyl;
$R_4$ is hydrogen, halogen, —$NR_5 R_6$, —$S(O)_m R_7$, alkyl, haloalkyl, —$OR_8$ or each of $R_5$ and $R_6$, which are the same or different, is hydrogen, alkyl, haloalkyl, —C(O)alkyl or —$S(O)_r CF_3$; or $R_5$ and $R_6$ together form a divalent lower alkylene radical which is optionally interrupted by one or more heteroatoms selected from O, S and N;
$R_7$ is alkyl or haloalkyl;
$R_8$ is alkyl, haloalkyl or hydrogen;
$R_9$ is hydrogen or alkyl;
$R_{10}$ is phenyl or heteroaryl, each of which is unsubstituted or is substituted with one or more substituents selected from the group consisting of hydroxy, halogen, —O—alkyl, —S—alkyl, cyano and alkyl;
each of $R_{11}$ and $R_{12}$, which are the same or different, is halogen or hydrogen;
$R_{13}$ is halogen, haloalkyl, haloalkoxy, —$S(O)_q CF_3$ or —$SF_5$;
each of m, n, q and r, which are the same or different, is 0, 1 or 2; and
X is nitrogen or C—$R_{12}$;
provided that when $R_1$ is methyl, $R_3$ is haloalkyl, $R_4$ is $NH_2$, $R_{11}$ is Cl, $R_{13}$ is $CF_3$, and X is N;
which]
*wherein the compound is 5-amino-3-cyano-1-(2,6-dichloro-4-trifluoromethyl)phenyl-4-trifluoromethylsulfinylpyrazole;*

*and* is effective both as an attractant and as an insecticide *without additional attractant components.*

32. A method according to claim 30, wherein the food source comprising said compound [of formula (I)] is in solid form.

33. A method according to claim 32, wherein said solid form is a solid bait, *said bait comprising said compound and ingredients that can be eaten by insects, but said bait does not contain an additional attractant.*

35. A method according to claim 30, wherein said compound [of formula (I)] is offered in an amount of from about 0.00001 g to about 20 g per 100 square meters.

36. A method according to claim 35, wherein said compound [of formula (I)] is offered in an amount of from about 0.001 g to about 1 g per 100 square meters.

\* \* \* \* \*